United States Patent [19]

Smiley et al.

[11] Patent Number: 4,508,505
[45] Date of Patent: Apr. 2, 1985

[54] MAGNETIC ORTHODONTIC TORQUING APPLIANCE

[75] Inventors: Harry Smiley, White Plains; Abraham Blechman, Tappan, both of N.Y.

[73] Assignee: Medical Magnetics, Inc., Ramsey, N.J.

[21] Appl. No.: 548,616

[22] Filed: Nov. 4, 1983

Related U.S. Application Data

[63] Continuation-in-part of Ser. No. 322,423, Nov. 18, 1981, Pat. No. 4,424,030, which is a continuation of Ser. No. 19,427, Mar. 12, 1979, abandoned.

[51] Int. Cl.³ .............................................. A61C 7/00
[52] U.S. Cl. ..................................................... 433/18
[58] Field of Search ........................................... 433/18

[56] References Cited

U.S. PATENT DOCUMENTS 4,017,973  4/1977  Nelson ................................. 433/18
4,424,030  1/1984  Smiley ................................. 433/18

Primary Examiner—Robert Peshock
Attorney, Agent, or Firm—Hopgood, Calimafde, Kalil, Blaustein & Judlowe

[57] ABSTRACT

The invention contemplates configurations of permanently magnetized magnetic elements adapted for fixation to different teeth for so torsionally reacting with each other as to apply continuous unidirectional torque as needed for particular orthodontic applications. The magnetic reaction responsible for such torque development is also instrumental in providing an environment for concurrent development of osteogenesis and soft-tissue repair, in aid of the orthodontic displacement process.

13 Claims, 8 Drawing Figures

U.S. Patent   Apr. 2, 1985   4,508,505
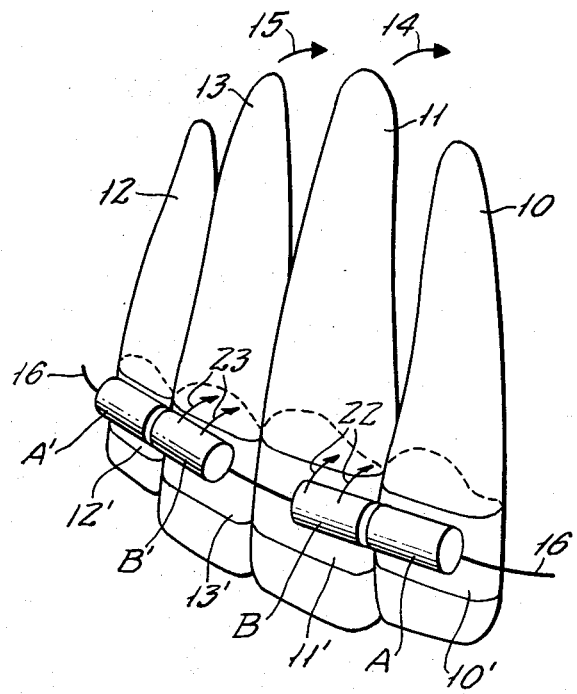
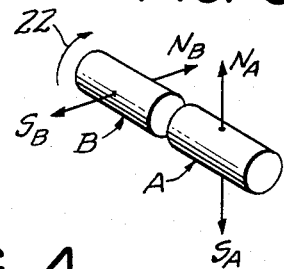
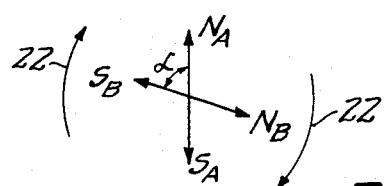
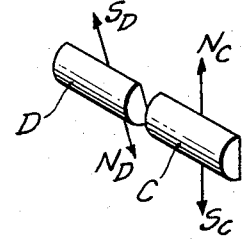
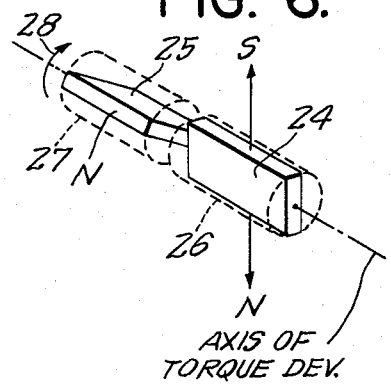
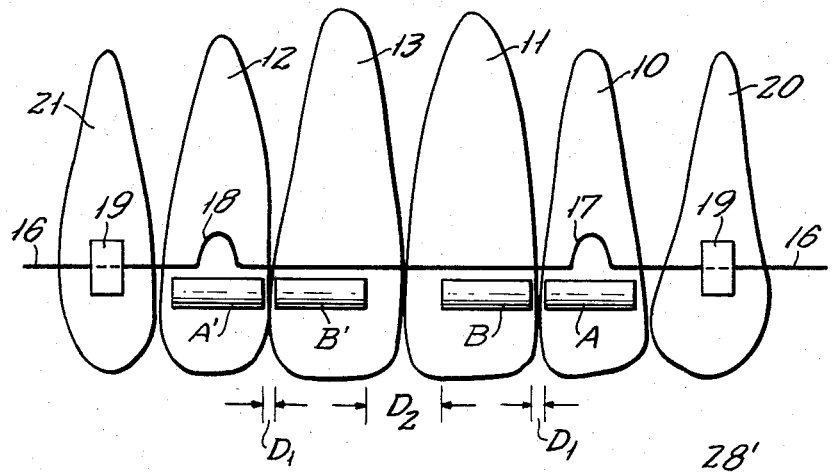
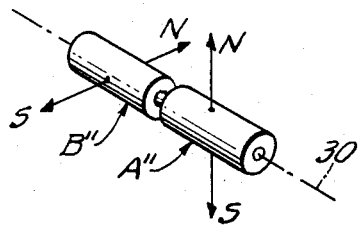
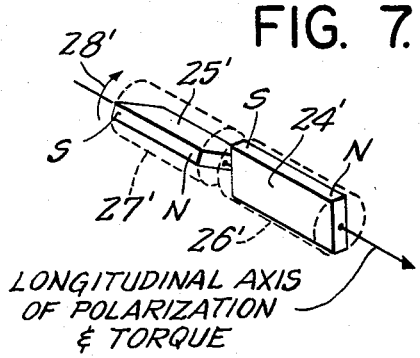

MAGNETIC ORTHODONTIC TORQUING APPLIANCE

BACKGROUND OF THE INVENTION

This application is a continuation-in-part of our copending application Ser. No. 322,423, filed Nov. 18, 1981, now U.S. Pat. No. 4,424,030, issued Jan. 3, 1984, which is a continuation of our original application, Ser. No. 19,427, filed Mar. 12, 1979 (now abandoned).

Said applications disclose various embodiments of magnetic osteogenic and orthodontic appliances, in which relative movement of magnetic devices produces varying currents in localized regions in aid of soft-tissue repair and osteogenesis. Some of the disclosed arrangements utilize magnetic devices for essentially only orthodontic purposes, while others are primarily adapted for soft-tissue repair and osteogenesis. Among the disclosed arrangements is an orthodontic technique for imparting a torquing effect on anterior teeth. According to the disclosed technique, an orthodontic archwire, suitably mounted to extend across the labial regions of anterior teeth, supports a plurality of polarized magnetic modules thereon, with their respective polarization axes arranged to impart a desired twisting or torquing action to one or more teeth with respect to adjacent or nearby teeth. More specifically, as disclosed, the magnetic modules are attached to orthodontic bands on the labial aspect of upper anterior teeth, in conjunction with an archwire which is ligated to the teeth. The resultant magnetic torquing is imparted to the teeth, causing lingual root torque.

BRIEF STATEMENT OF THE INVENTION

It is an object of the invention to provide improved and further magnetic torquing devices and arrangements of the character indicated.

It is a specific object to meet the above object with means whereby therapeutically beneficial varying magnetic fields may be produced, in the course of orthodontic torquing and as an aid to soft-tissue in a region of torque-generated tooth displacement.

Another object is to achieve the above objects with non-invasive structure adapted for fixation to involved teeth.

In preferred arrangements, the invention achieves the foregoing objects with generally cylindrical magnet elements which are respectively fixed to adjacent teeth, with their cylindrical axes aligned and closely spaced at adjacent end faces for torque-developing reaction between these end faces. In one form, permanent polarization of each magnet is transverse to the cylindrical axis, and the relative orientation of the mounted magnet elements is characterized by such an angular difference that torquing about the cylindrical axis is maximum, and attraction or repulsion across the gap between end faces is minimal. In another form, each magnetic element comprises a rectangular prismatic magnet part which is embedded in a non-magnetic cylindrical body part; the major transverse dimension of the magnet part is substantially the body diameter, and the minor transverse dimension of the magnet part is much less than the body diameter, so that, when polarized in the direction of the cylindrical axis, like or opposed polarities at adjacent pole faces will develop torque about the cylindrical axis, to the extent that the respective major transverse dimensions of the respective pole faces differ by less than 90 degrees.

DETAILED DESCRIPTION

The invention will be illustratively described in detail in conjunction with the accompanying drawings, in which:

FIG. 1 is a simplified view in perspective, showing the torquing effect of magnets of the invention, in application to upper anterior teeth;

FIG. 2 is a developed view in front elevation to further illustrate the invention, in the context of adjacent canine teeth;

FIG. 3 is a diagrammatic view in perspective to illustrate magnetic polarization in one pair of the magnetic elements of FIG. 1 or FIG. 2;

FIG. 4 is a diagram to illustrate an angular relation between polarized orientations in FIG. 3; and FIGS. 5, 6, 7 and 8 are views similar to FIG. 3 to show further embodiments.

In FIG. 1, the invention is shown in application to the labial aspect of upper anterior teeth, namely, left lateral and central incisors 10–11, and right lateral and central incisors 12–13. Orthondontic bands for each of these teeth are identified by the same reference numbers, with primed notation; these bands are conventional (e.g., of stainless steel and, therefore, non-magnetic) and are conventionally secured to their respective teeth.

For purposes of illustrative discussion, it will be assumed that the orthodontic problem to be solved by the invention is to generate and continuously apply torque to both central incisors 11–13 for corrective displacement of the root ends thereof in the posterior direction, as indicated by arrows 14–15, and at the same time to retain both lateral incisors 10–12 against displacement. To this end, an orthodontic archwire 16 is suitably mounted to extend across the lower ends of the anterior teeth and will be understood to similarly traverse lower ends of buccal sides of further adjacent teeth; wire 16 will be understood to be secured in conventional fashion to plural adjacent teeth, to both the right and left sides of the anterior teeth of FIG. 1. Since the lateral incisors 10–12 are not to be displaced, wire 16 will be understood further to be secured to each of these lateral incisors; preferably, and as better shown in FIG. 2, a vertical loop 17 (18) is formed in archwire 16 at registry with each of the respective lateral incisors 10 (12), so that in bonding each such loop to the labial aspect of the involved tooth, a strong anti-torquing reference is established for retaining both lateral incisors against displacement. Also shown in FIG. 2 are plate or bracket means 19 by which the archwire 16 is illustratively secured to adjacent teeth, such as canines 20–21.

In accordance with the invention, a first pair of torsionally reacting permanent magnet elements A-B is mounted to the left incisors 10–11, and a second such pair A'-B' is similarly mounted to the right incisors 12–13. The magnetic elements A-B and A'-B' are cylindrical, suitably of SmCo and bio-compatibly sheathed or coated, as with a thin application of Paralyne, a non-pourous polymer product of Union Carbide. Bonding of the magnetic elements to their respective teeth is via suitable composite bonding material, such as the preparation "Right On", a product of TP Laboraories, Laporte, Ind. As shown in FIG. 2, the reacting magnet pair A-B is mounted for alignment of the respective cylindrical axes, at short axial separation $D_1$, in the order of 1 mm; the same closely spaced relation applies for magnets of the other pair A'-B', but the gap $D_2$ between adjacent magnetic elements B-B' of the respective pairs is substantially greater, e.g., 2.5 to 3.0 mm, in order to avoid torsional reaction between elements B-B'.

FIG. 3 is a simplified diagram to explain polarized orientation of magnetic elements of the pair A-B, and, subject to a mirror reversal of components and polarized reactions, the same explanation is applicable for the pair A'-B'. In FIG. 3, the fixed or reference magnet A is polarized transverse to the cylindrical axis, being shown polarized vertically, with North up and South down, whereby the North pole is along the upper diametral intercept of the cylinder with a vertical geometric plane which includes the cylinder axis, and the South pole is along the lower diametral intercept of the cylinder with the same plane. This being the case, the end faces of magnet A are polarized with poles at opposite ends of a vertically oriented diameter. In similar fashion, magnetic element B is also polarized transversely of its cylindrical axis, but the polarized direction is generally horizontal, so that the end faces of magnet B are characterized by poles at opposite ends of a generally horizontally oriented diameter. In FIG. 4, the angle $\alpha$ designates the angular spread between these differently oriented magnetically polarized directions, both of which are transverse to the cylinder axis.

The reaction between adjacent end faces of magnet elements A-B will be seen to be virtually purely torsional and, since magnet A is relatively fixed (to the exclusion of magnet B), magnet B torsionally reacts in the clockwise sense (as viewed in FIGS. 3 and 4), as suggested by arrows 22, in that this is the direction of attraction between opposite poles $N_A$-$S_B$ and $N_B$-$S_A$ (and also of repulsion between like poles $N_A$-$N_B$ and $S_A$-$S_B$) at the adjacent end faces of magnets A-B. In FIG. 1, due to perspective viewing, it is not possible to show more than arrows 22 on the labial side, but these arrows will be understood to indicate torque reaction operative continuously on magnet B, about its cylindrical axis, and in the direction to continuously urge the root displacement for tooth 11 in the desired direction 14; in similar fashion, arrows 23 will be understood to indicate torque reaction operative continuously on magnet B', about its cylindrical axis, and in the direction continuously urging root displacement for tooth 13 in the desired direction 15.

FIG. 5 is a schematic indication that the prismatic shape of the respective magnets C-D of a given torsionally reacting pair need not be purely cylindrical. The magnets C-D happen to be semicylindrical, for less bulk in the labial region of involved teeth. And the flat side of each half cylinder will be seen as an aid to mounting effectiveness, as to orthodontic bands 10'-11'. The respective transverse planes of permanent polarization are designated by arrow symbolism as in FIG. 3, and mountings of the magnets to their respective teeth should be such as to develop an angle $\alpha$ therebetween.

FIG. 6 is a schematic indication that magnet parts 24 (25) of torsionally reacting magnetic modules or elements may be rectangularly prismatic, the remainder of each module being a body part 26 (27) of bio-compatible non-magnetic material, which may be cylindrical, truncated cylindrical, or otherwise for the patient's comfort. The magnet part 24 is shown permanently polarized in the direction of its major dimension transverse to the cylindrical axis, and this major dimension may be substantially the full diametral extent of the body part 26 in which it is embedded, while the minor transverse dimension of magnet part 24 is substantially less than the major transverse dimension. Similar proportions and polarizing may characterize magnet part 25 embedded in body part 27, but the angle between polarization planes is again $\alpha$, consistent with discussion above. If magnet 24 and its body part 26 are fixed, then for the symbolism and relationship shown, magnet 25 and its body part 27 will be continuously urged clockwise (in the sense of arrow 28), by reason of torque reaction between adjacent end faces of magnet parts 24-25 and about the cylinder axis.

In FIG. 7, parts physically appear to resemble but are not the same as those of FIG. 6 and have therefore been given the same reference numbers, with primed notation. The difference lies in the fact that the magnet parts 24'-25' of FIG. 7 are polarized in the longitudinal direction of the cylinder axis. If magnet 24' and its body part 26' are fixed (as to tooth 10), then for the opposite-pole arrangement shown at the gap between magnets 24'-25', torque reaction about the longitudinal axis continuously urges magnet 25' and its body part 27' clockwise, as suggested by arrow 28'. If on the other hand, like polarities appear at adjacent end faces of magnets 24'-25', the torque reaction is counterclockwise.

The invention will be seen to achieve all stated objects and will be seen to be applicable to torquing situations other than the anterior tooth situation of FIGS. 1 and 2. For example, the invention is applicable to lingual-aspect use and to buccal-aspect use for teeth other than those of the anterior set, and whether upper or lower teeth are to be orthodontically reset by magnetic-torque reaction. Further, the described devices lend themselves to sustained retention in installed position, so that in the course of eating, gnawing, gnashing or the like normal or nervous tooth-displacing movements peculiar to a given patient, there will necessarily be a transiently stressed displacement of involved teeth, including the adjacent teeth undergoing magnetic-torquing treatment. Any such transient displacement necessarily transiently alters the gap between adjacent ends of coacting adjacent magnets, thus giving rise to corresponding transient changes in the magnetic-flux field attributable to the reacting polarized magnets and surrounding the same. Such external field and flux changes therein give rise to non-invasive osteogentic and soft-tissue repair action in the greater volume which includes the involved teeth and their root regions, all of which is in aid of permanently setting a torque-displaced root in its new orientation. This action and process are more fully explained in our said application Ser. No. 322,423, and the action and repair process continue throughout the period of orthodontic torquing.

While the invention has been described in detail for several embodiments, it will be understood that modifications may be made without departing from the scope of the invention. For example, the cylindrical magnets of FIGS. 1, 2 and 3 need not be solid cylindrical, an annular configuration being shown in FIG. 8 for each of the magnets A"-B". The central elongate bore of each of the magnets A"-B" may be sized for free reception of an inserted archwire 30, thus facilitating correct axial alignment and spacing of magnets A"-B" in the process of bonding them to the respective associated teeth 10-11.

What is claimed is:

1. Orthodontic torquing means, comprising a pair of permanently polarized elongate cylindrical magnet elements, each magnet element being oppositely polarized at the respective diametral intercepts of a geometric plane which includes the cylindrical axis of the element, whereby a circular end face of the element is characterized by a polarization diameter normal to the cylindrical axis, one magnet element being adapted for fixation to an exposed face of one tooth and the other magnet element being adapted for fixation to the exposed face of an adjacent tooth, (a) with their cylindrical axes in substantial alignment and (b) with a gap between said magnet elements and (c) with the polarization diameters of adjacent end faces of said magnet elements at orientations which differ by at least 45 degrees, whereby in reaction to their polarized orientation a unidirectional torque about the cylindrical axes may be continuously applied to one of said teeth with respect to the other of said teeth, and bio-compatible non-magnetic means encasing each of said magnet elements.

2. The torquing means of claim 1, in combination with an archwire adapted to span the faces of said one tooth and said adjacent tooth and also to span the faces of a plurality of teeth on opposite sides of said one tooth and said adjacent tooth, and means for securing said archwire to teeth other than said one tooth.

3. The torquing means of claim 1, in which each magnet element comprises a polarized rectangular prismatic magnet part centered on the cylindrical axis, said bio-compatible means being a non-magnetic elongate cylindrical body part in which the magnet part is embedded for substantially the longitudinal extent thereof.

4. The torquing means of claim 3, in which the major transverse dimension of said magnet part is substantially the diametral extent of said body part, and the minor transverse dimension of said magnet part being substantially less than said diameter.

5. The torquing means of claim 1, in which said cylindrical magnet elements are truncated-cylindrical, the truncation being in a plane parallel to the cylindrical axis.

6. Orthodontic torquing means, comprising a pair of permanently polarized elongate cylindrical magnet elements, each magnet element comprising a polarized rectangular prismatic magnet part centered on the cylindrical axis, and a bio-compatible non-magnetic elongate cylindrical body part in which the magnet part is embedded for substantially the longitudinal extent thereof, the major transverse dimension of said magnet part being substantially the diametral extent of said body part, and the minor transverse dimension of said magnet part being substantially less than said diameter, one magnet element being adapted for fixation to an exposed face of one tooth and the other magnet element being adapted for fixation to the exposed face of an adjacent tooth, (a) with their cylindrical axes in substantial alignment and (b) with a gap between said magnet parts and (c) with the major transverse dimensions of said magnet parts at orientations which differ by at least 45 degrees.

7. Orthodontic torquing means according to claim 6, in which the polarization of each of said magnet parts is longitudinal along the cylindrical axis.

8. Orthodontic torquing means according to claim 6, in which the polarization of each of said magnet parts is transverse to the cylindrical axis and along the major dimension of the magnet part.

9. Orthodontic torquing means according to claim 1, in which each of said magnet elements has a central bore adapted for assembly to an archwire.

10. Orthodontic torquing means, comprising a pair of permanently polarized magnet elements each of which is adapted for mounting to a different one of two adjacent teeth, said magnet elements being rectangular prismatic and each magnet element being polarized in the direction of a plane normal to two opposed sides of the magnetic element, the mounting for each tooth being such that (a) an axis of relative torque development is established through both magnet elements substantially in both said planes and parallel to said two opposed sides of each magnet element, (b) adjacent other sides of said magnets are in relatively close reacting adjacency, and (c) said respective planes are in an acute-angle relationship in terms of their respective orientations about the axis of relative torque development.

11. Orthodontic torquing means according to claim 10, in which said acute-angle relationship is in the order of 45 degrees.

12. Orthodontic torquing means, comprising a pair of permanently polarized magnet elements each of which is adapted for mounting to a different one of two adjacent teeth, said magnet elements being rectangular prismatic and each magnet being polarized in the direction of a plane normal to two opposed sides of the magnetic element, the mounting for each tooth being such that (a) an axis of relative torque development is established through both magnet elements substantially in both said planes and perpendicular to said two opposed sides of each magnet element, (b) adjacent other sides of said magnets are in relatively close reacting adjacency, and (c) said respective planes are in an acute-angle relationship in terms of their orientations about the axis of relative torque development.

13. Orthodontic torquing means according to claim 12, in which said acute-angle relationship is in the order of 45 degrees.

* * * * *